US012515014B2

United States Patent
(12) United States Patent
Wu et al.

(10) Patent No.: US 12,515,014 B2
(45) Date of Patent: Jan. 6, 2026

(54) SELF-EXPANDING CANNULA

(71) Applicants: UNIVERSITY OF MARYLAND, BALTIMORE, Baltimore, MD (US); UNIVERSITY OF MARYLAND, BALTIMORE COUNTY, Baltimore, MD (US)

(72) Inventors: Zhongjun Wu, Marriottsville, MD (US); Bartley P. Griffith, Gibson Island, MD (US); Jun Ding, Catonsville, MD (US)

(73) Assignees: UNIVERSITY OF MARYLAND, BALTIMORE, Baltimore, MD (US); UNIVERSITY OF MARYLAND, BALTIMORE COUNTY, Baltimore County, MD (US)

( * ) Notice: Subject to any disclaimer, the term of this patent is extended or adjusted under 35 U.S.C. 154(b) by 812 days.

(21) Appl. No.: 17/142,375

(22) Filed: Jan. 6, 2021

(65) Prior Publication Data

US 2021/0121659 A1 Apr. 29, 2021

Related U.S. Application Data

(62) Division of application No. 14/905,073, filed as application No. PCT/US2014/046978 on Jul. 17, 2014, now Pat. No. 10,912,920.

(Continued)

(51) Int. Cl.
*A61M 25/00* (2006.01)
*A61M 1/36* (2006.01)
*A61M 25/04* (2006.01)

(52) U.S. Cl.
CPC ........ *A61M 25/003* (2013.01); *A61M 1/3659* (2014.02); *A61M 2025/0024* (2013.01);
(Continued)

(58) Field of Classification Search
CPC ........ A61M 25/003; A61M 2025/0031; A61M 25/005; A61M 2025/0024; A61M 2025/0039; A61M 2025/0059
See application file for complete search history.

(56) References Cited

U.S. PATENT DOCUMENTS 4,581,017 A * 4/1986 Sahota ................ A61M 25/104
606/192
4,830,023 A * 5/1989 de Toledo ....... A61M 25/09033
600/585

(Continued)

*Primary Examiner* — Courtney B Fredrickson
(74) *Attorney, Agent, or Firm* — Whiteford, Taylor & Preston, LLP; Gregory M. Stone

(57) ABSTRACT

Disclosed is a self-expanding cannula, systems using such cannulae, and methods of their use. The cannulae may comprise single lumen cannula ("SLC") configurations and double lumen cannula ("DLC") configurations, and include at least a first cannula and a self-expanding wire frame attached to the first cannula. Self-expanding wire frame is automatically expandable from a compressed state (providing a reduced cannula diameter as it is moved through a patient's body to the site at which it is to be deployed) to an expanded state (which increases the diameter of the cannula to the diameter intended for its normal use). The expanded wire frame provides radial support to prevent a drainage canal (whether a patient's blood vessel or a portion of the system inserted into the patient's blood vessel) from collapsing as fluid is drained from the patient.

17 Claims, 10 Drawing Sheets

Related U.S. Application Data

(60) Provisional application No. 61/847,638, filed on Jul. 18, 2013.

(52) U.S. Cl.
CPC ............... *A61M 2025/0031* (2013.01); *A61M 2025/0035* (2013.01); *A61M 2025/0039* (2013.01); *A61M 25/005* (2013.01); *A61M 2025/0059* (2013.01); *A61M 25/04* (2013.01); *A61M 2205/0266* (2013.01)

(56) References Cited

U.S. PATENT DOCUMENTS

| | | | | |
|---|---|---|---|---|
| 4,909,252 | A * | 3/1990 | Goldberger | A61M 25/104 604/103.1 |
| 6,042,597 | A * | 3/2000 | Kveen | A61F 2/915 623/1.15 |
| 6,673,042 | B1 * | 1/2004 | Samson | A61M 29/02 606/198 |
| 2001/0044598 | A1 * | 11/2001 | Parodi | A61B 17/22 604/104 |
| 2003/0040704 | A1 * | 2/2003 | Dorros | A61B 17/3207 604/509 |
| 2007/0250148 | A1 * | 10/2007 | Perry | A61F 2/915 623/1.22 |
| 2011/0190683 | A1 * | 8/2011 | Gellman | A61M 25/0023 606/191 |
| 2011/0218609 | A1 * | 9/2011 | Chobotov | A61F 2/06 623/1.2 |

* cited by examiner

SELF-EXPANDING CANNULA

CROSS-REFERENCE TO RELATED APPLICATIONS

This application is a divisional of co-pending and co-owned U.S. patent application Ser. No. 14/905,073 entitled "Self-Expanding Cannula," filed with the United States Patent and Trademark Office on Jan. 14, 2016, which application is a national stage entry of international PCT Application Serial No. PCT/US14/46978 entitled "Self-Expanding Cannula," filed with the United States Patent and Trademark Office on Jul. 17, 2014, which application is based upon and claims priority from U.S. Provisional Patent Application Ser. No. 61/847,638 entitled "Self-Expanding Cannula," filed with the U.S. Patent and Trademark Office on Jul. 18, 2013, all by the inventors herein, the specifications of which are incorporated herein by reference in its entirety.

FIELD OF THE INVENTION

The present invention relates generally to medical devices, and more particularly to cannulas, systems using cannulas and methods for their use.

BACKGROUND OF THE PRIOR ART

As preliminary background, blood circulation in a person's heart is described here to provide a better understanding of certain aspects of embodiments of the invention as set forth herein. In that regard, FIG. 1 is a diagram of a heart 10 and the circulatory flow within the heart. Blood travels to the heart from the upper part of the body through the superior vena cava ("SVC") 28, and from the lower part of the body through the inferior vena cava ("IVC") 29, into the right atrium 34. A one-way valve, called the Eustachian valve (not shown), resists blood flow from the right atrium back into the IVC. The right atrium contracts to force blood through the tricuspid valve 35 and into the right ventricle 36, which in turn contracts to force blood through the pulmonary valve 37 and into the pulmonary artery 30. The pulmonary artery 30 directs blood to the lungs, where the blood is oxygenated.

After the blood is oxygenated in the lungs, it returns to the heart through the pulmonary vein 43 and into the left atrium 47. The left atrium 47 contracts to push the blood through the mitral valve 48 and into the left ventricle 41. The left ventricle 41 then pumps the blood into the aorta 38, which then distributes the blood to the greater arteries to be carried out to the rest of the body.

Blood flow in a person's body, and particularly the oxygen carried by that person's blood as it courses through their body, is adversely affected by heart failure and lung disease, both of which are pervasive killers.

Heart failure occurs when the heart cannot pump sufficient blood to meet the needs of the body. Heart failure affects 5.7 million patients in the U.S., and it contributed to almost 280,000 deaths in 2008 (Roger et al., Circulation, 2012; 125(1):e2:-220). The condition creates a major burden on health care providers and is expensive to treat. The estimated direct and indirect costs of heart failure in the U.S. for 2010 was $39.2 billion (2010 Heart Failure Fact Sheet from Centers for Disease Control and Prevention). Despite advances in medical care, the prognosis for patients with heart failure remains poor, especially when in advanced stages. Patients with advanced heart failure often require ventricular assist device ("VAD") support or heart transplantation to survive. Of course, heart transplantation is limited by a limited supply of donor organs. VAD's, on the other hand, are mechanical pumps designed to augment or replace the function of one or more chambers of the failing heart, and may be used where heart transplantation is not a viable or desirable option. While use of VAD's is increasing, it nonetheless remains limited due to the need for major operative intervention.

Likewise, lung disease is the number three killer in the U.S., responsible for 1 in 6 deaths (American Lung Association). 400,000 deaths annually are attributed to pulmonary causes in spite of $154 billion in expenditures to fight lung disease (Sanovas, "Lung Disease"). Chronic obstructive pulmonary disease ("COPD") is one of the most common lung diseases, and is the fourth leading cause of death in the U.S. Moreover, Adult Respiratory Distress Syndrom ("ARDS") commonly afflicts 190,000 patients yearly, and the average survival is between only 30-50%. If a patient's lungs do not function properly (e.g., due to COPD or ARDS), the oxygenation of blood is not sufficient. In order to compensate for such lack of oxygen, Extracorporeal Membrane Oxygenation ("ECMO") may be used.

In clinical practice, the use of VAD's and ECMO each requires major invasive surgical procedures to implant the devices via a set of cannulae. A cannula is a medical tube inserted into the body for drainage and/or infusion of fluids, and in the case of VAD and ECMO, the drainage and/or infusion of blood. Because of the major invasive nature of the procedures for implanting those devices, only a limited population of patients receives these device-based therapies. The major problems of available cannulae for ECMO (as described in U.S. Pat. No. 7,473,239 to Wang et al., the specification of which is incorporated herein by reference in its entirety) include: (1) multiple cannulation and insertion of cannulae with larger diameters causing extra trauma to patients; (2) blood recirculation leads to insufficient extracorporeal oxygenation; and (3) the placement of the drainage lumen causes insufficient venous blood drainage. Similarly, cannulation technologies used in VAD's share at least the problem of causing extra trauma to patients.

Accordingly, there is a need in the art for a device, systems, and methods that will reduce the trauma associated with the use of VAD's and ECMO, that will minimize the risk of blood recirculation, and that will ensure sufficient venous blood drainage, and that particularly will offer a minimally invasive, efficient, and simple percutaneous cannula system for use with VAD and ECMO procedures.

DESCRIPTION OF THE INVENTION

Disclosed herein is a novel, self-expanding cannula, systems using such cannulae, and methods of their use. The cannulae may comprise single lumen cannula ("SLC") configurations and double lumen cannula ("DLC") configurations. The cannula includes at least a first cannula and a self-expanding wire frame attached to the first cannula. The self-expanding wire frame may, for example, be temperature-responsive to expand from a compressed state (providing a reduced cannula diameter as it is moved through a patient's body to the site at which it is to be deployed) to an expanded state (which increases the diameter of the cannula to the diameter intended for its normal use) in response to warming of the wire frame, such as from the patient's own body temperature. Alternatively, the wire frame may have sufficient flexibility so as to allow it to be radially compressed (such as by inserting the wire mesh and cannula to which it is attached into a tearable sheath for initial insertion into a patient's blood vessel) and thereafter return to its expanded, normal diameter after such radial compression is removed. The expanded wire frame provides radial support to prevent a drainage canal (whether a patient's blood vessel or a portion of the system inserted into the patient's blood vessel or other portion of the patient's body) from collapsing as fluid is drained from the patient.

With regard to certain aspects of the invention (in a DLC configuration), the first cannula may comprise a drainage cannula with the wire frame extending outward from a distal end of the drainage cannula. A port is located in a sidewall of the drainage cannula, which port receives a second cannula. The second cannula is an infusion cannula and extends through the distal end of the first cannula, and through and out of the distal end of the wire frame, and is longitudinally movable within the first cannula and the wire frame.

With regard to further aspects of the invention (in a SLC configuration), the first cannula may comprise a drainage cannula again with the wire frame extending outward from a distal end of the drainage cannula, but without a port in a sidewall of the drainage cannula and without a second cannula.

With regard to still further aspects of the invention (and in another DLC configuration), the first cannula may comprise a drainage cannula having the wire frame embedded within a distal end of the drainage cannula (i.e., embedded within the circumferential wall of the drainage cannula at its distal end). A second cannula is an infusion cannula and includes a port located in a sidewall of the infusion cannula, which port receives the first drainage cannula. The first drainage cannula extends through the distal end of the second infusion cannula and is longitudinally moveable within the second infusion cannula.

With regard to still further aspects of the invention, the foregoing configurations may comprise components of a fluid handling system for a patient's blood, and particularly for suctioning, oxygenating, and infusing a patient's blood, along with a delivery mechanism for placement of the cannulae in the patient's body.

An SLC employing aspects of the invention may be pre-packaged or assembled in a small sheath, and includes a self-expanding wire frame that expands into the preset, intended dimension after it is deployed in a patient, in turn radially supporting the SLC and the blood vessel in which it is positioned. The SLC may be used as venous and arterial cannulae.

Likewise, a DLC employing aspects of the invention comprises a drainage cannula that forms a drainage lumen and an infusion cannula that forms an infusion lumen. The DLC may be used for percutaneous cannulation for Veno-PA and Veno-RV ECMO, and for LV-Aortic mode LVAD support. For the Veno-PA mode, the great vein (the SVC or the IVC) itself is used by the DLC as forming a part of the drainage lumen, and is supported by a self-expanding wire frame that prevents the vein from collapsing while drawing venous blood at the vessel insertion site. The venous blood is drained from the drainage cannula by a blood pump and is sent to an oxygenator for oxygenation. The infusion cannula of the DLC is a thin-wall, preferably polyurethane tube that returns oxygenated blood directly to the PA. The infusion cannula preferably has a wire-reinforced tip, and has a smaller diameter than the drainage cannula so that it may be placed inside of and move within the drainage lumen. The Veno-RV mode is similar to the Veno-PA mode, except that the oxygenated blood will be returned to the right ventricle instead of the PA. For both Veno-RV and Veno-PA modes, the DLC may be inserted from the jugular vein, the subclavian vein, or the femoral vein. For the LV-Aortic mode LVAD support, the DLC may be inserted from the ascending aorta by a minimally invasive surgical procedure. The wire reinforced drainage lumen of the DLC draws blood from the left ventricle, and its infusion lumen returns the blood to the ascending aorta. The DLC's drainage lumen has a smaller diameter than the infusion lumen so that it may be placed inside of and move within the infusion lumen.

The SLC assembly, the DLC assembly, and their own delivery systems are described herein. Additionally, procedures for delivering the SLC and DLC assemblies into vessels are also described herein.

BRIEF DESCRIPTION OF THE DRAWINGS

The numerous advantages of the present invention may be better understood by those skilled in the art by reference to the accompanying figures in which.

BEST MODE(S) FOR CARRYING OUT THE INVENTION

The invention summarized above may be better understood by referring to the following description, claims, and accompanying drawings. This description of an embodiment, set out below to enable one to practice an implementation of the invention, is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

Figure 1:
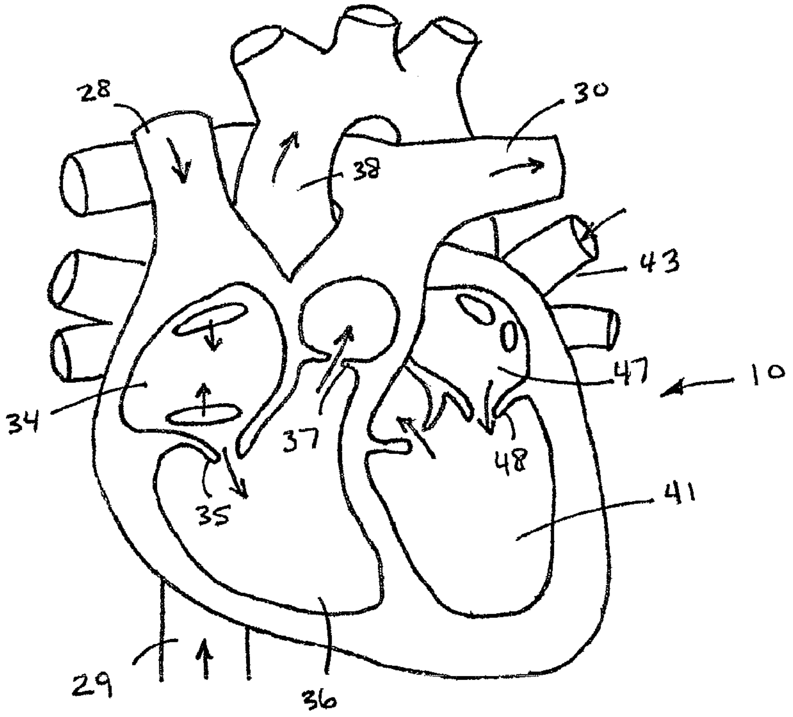
FIG. 1 is a diagrammatic view of a heart and reflecting the circulation path of blood though the heart.
Figure 1A:
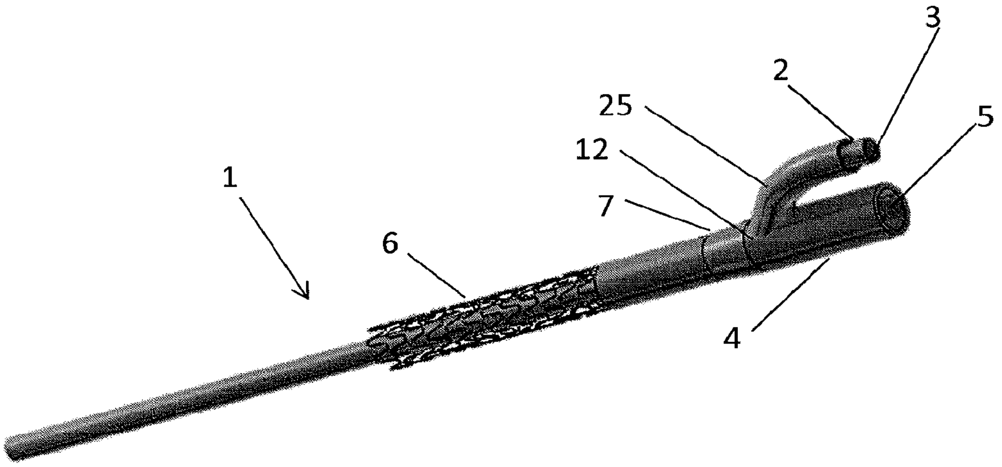
FIG. 1A is a perspective view of a DLC assembly according to aspects of the present invention.
Figure 1B:
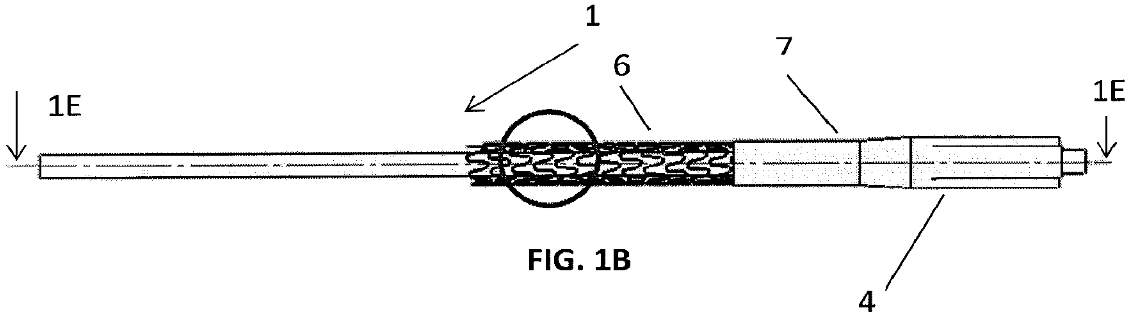
FIG. 1B is a top view of the DLC assembly of FIG. 1A.
Figure 1C:
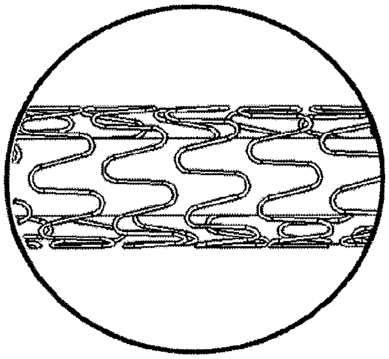
FIG. 1C is a partial enlarged view of the wire frame and the infusion cannula of FIG. 1B.
Figure 1D:
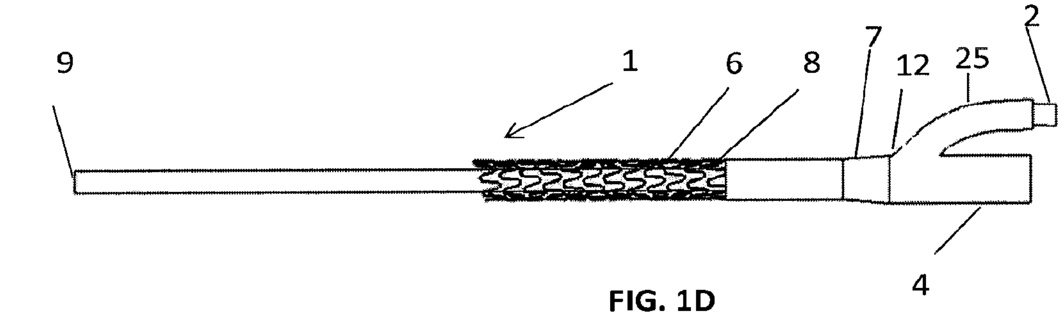
FIG. 1D is a side view of the DLC assembly of FIG. 1A.
Figure 1E:
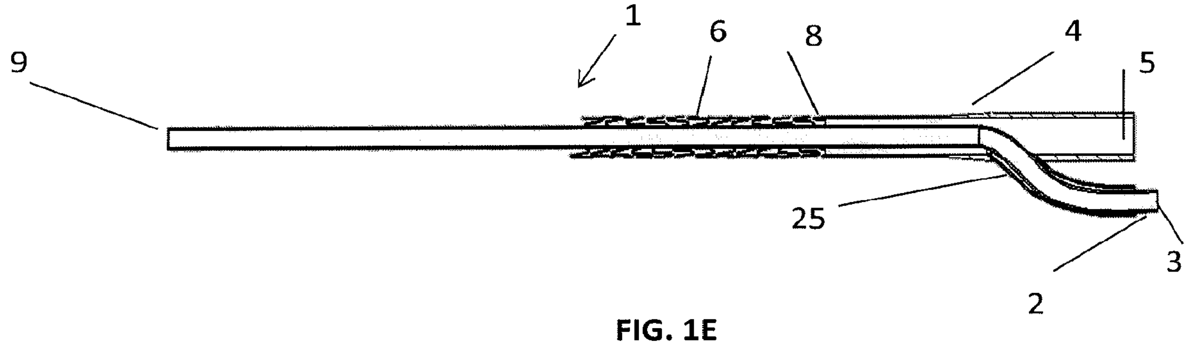
FIG. 1E is a cross-sectional view of the DLC assembly of FIG. 1B.

In accordance with certain aspects of an embodiment of the invention, a DLC assembly is shown in FIGS. 1A through 1E, in which like numerals reflect like parts. FIG. 1A is a perspective view of the DLC assembly 1, FIG. 1B is a top view of the DLC assembly 1, FIG. 1C is a partial, enlarged view of the wire frame 6 and the infusion cannula 2 of DLC assembly 1, FIG. 1D is a side view of DLC assembly 1, and FIG. 1E is a cross-sectional view of DLC assembly 1. DLC assembly 1 includes a drainage cannula 4 and its wire frame body 6, a hollow infusion port 25, and an infusion cannula 2 having a circular solid body extending through the infusion proximal end to the distal end of drainage cannula 4. Infusion cannula 2 forms an infusion lumen 3. Likewise, drainage cannula 4 forms a drainage lumen 5. The infusion port 25 opens into drainage lumen 5 through the wall 12 of the drainage lumen 5. Infusion cannula 2 is sized and configured to move within infusion port 25, such that the position of an opening 9 of infusion cannula 2 at its distal end may be changed (with respect to drainage cannula 4), as is further detailed below. A self-expanding wire frame 6 is attached to the distal end of drainage cannula 4. Self-expanding wire frame 6 is preferably formed of a shape memory alloy that may be compressed to a diameter less than its intended diameter when in use inside of a patient's blood vessel, and that recovers to such intended diameter when warmed to its transition temperature as a result of the patient's own body temperature. In an embodiment of the invention, wire frame 6 is particularly formed from Nitinol, an allow typically made of approximately 55%-56% nickel and 44%-45% titanium by weight. Alternatively, self-expanding wire frame 6 may be sufficiently flexible so as to allow it to be radially compressed (such as by inserting the wire mesh and cannula to which it is attached into a tearable sheath for initial insertion into a patient's blood vessel, as further described below) and thereafter return to its expanded, normal diameter after such radial compression is removed. Further, in addition to Nitinol, self-expanding wire frame 6 may be formed of stainless steel or of shape-memory polymers, so longs as such configurations can be compressed and return to their original diameter or shape when the compressive force is removed.

The distal end of drainage cannula 4 may be formed having a tapered wall portion 7, and an end of wire frame 6 may be embedded in that tapered end 7 of drainage cannula 4. Alternatively, the distal end of drainage cannula 4 may be formed as a cylindrical passage having a smaller diameter of the proximal end of drainage cannula 4 with tapered wall portion 7 positioned between the distal end and the proximal end. In each case, wire frame 6 is preferably joined to the distal end of drainage cannula 4 by being molded into the plastic (e.g., polyurethane or any biocompatible plastic materials) wall of drainage cannula 4.

As used herein, the terms "distal" and "proximal" refer to respective distance from the person that is inserting the cannula into a patient. Thus and by way of example, from the perspective of FIG. 1D, the opening 9 is a distal opening of infusion cannula 2.

FIG. 1E is a cross-sectional view of DLC assembly 1. When DLC assembly 1 is inserted to the superior vena cava (SVC), venous blood from the SVC and from the inferior vena cava (IVC) is drained from the opening 8 of the drainage cannula 4. Usually, a negative pressure is applied when draining the venous blood. In prior art systems, the vein from which blood was being drawn would often collapse because of the pressure difference inside and outside of the vein. In accordance with an advantageous aspect of the invention, wire frame 6 supports the vein from collapsing. After the removal of such blood, it is processed and ultimately returns to the patient's body by infusion lumen 3 through opening 9.

As mentioned briefly above (and as will be discussed further below), infusion cannula 2 is longitudinally moveable within infusion port 35, drainage cannula 4, and wire frame 6. Moreover, infusion cannula 2 should have a length sufficient so that opening 9 of infusion cannula 2 may be positioned a sufficient distance away from the distal end of wire frame 6 so that opening 9 may reach at least into a patient's right ventricle, and preferably into a patient's pulmonary artery, when the distal end of wire frame 6 is positioned in the patient's SVC or IVC and with the opposite, proximal end of infusion cannula 2 still extending out from infusion port 25. This longitudinal separation of opening 9 of infusion cannula 4 from the distal end of wire frame 6 will help to minimize recirculation through drainage cannula 4 of freshly oxygenated blood that has already been returned to the patient through infusion cannula 2.

As mentioned above, in a particularly preferred embodiment, wire frame 6 may be formed of Nitinol, which is an alloy of nickel and titanium. Nitinol has a superelastic property, which refers to the ability to recover to its original shape above a certain temperature (i.e., its transformation temperature) after a deformation at a lower temperature. A process referred to as shape setting may be used to cause Nitinol to remember a desired shape. Usually, this process includes tightly constraining the material into the desired shape on a mandrel at 450-550° C. for 10-80 minutes, depending upon the particular Nitinol material being used (different Nitinol materials being available from different manufacturers), and the methods of carrying out such shape setting of Nitinol materials are known to those skilled in the art. In at least one embodiment, a preferred condition for heat treatment of a Nitinol wire suitable for use in the instant invention (readily commercially available from Johnson Matthey Inc., of West Chester, PA) and having a diameter of 0.01 inch in cross-section is 500° C. for 70 minutes, which can make its transformation temperature equal to preferably at least 27° C. In other embodiments, the Nitinol wire may be heat treated so that the transformation temperature can be between 30° C. and 37° C. (i.e., normal human body temperature). Below the transformation temperature, the material is not stable and its shape can be changed easily.

Figure 2A:
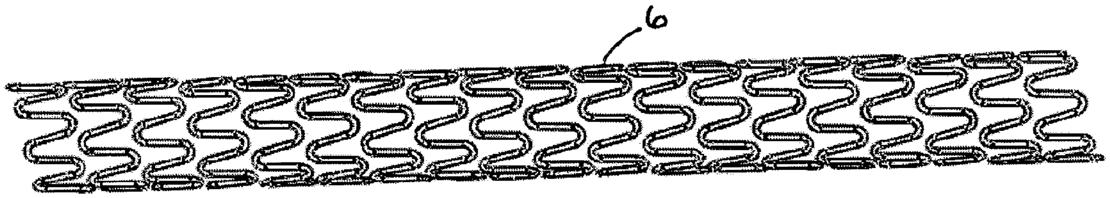
FIG. 2A is a cross-sectional view of a mid-plane of the wire frame according to aspects of the invention and shown in an expanded profile.
Figure 2B:
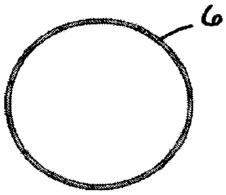
FIG. 2B is a transverse sectional view of the wire frame of FIG. 2A in an expanded profile.
Figure 2C:
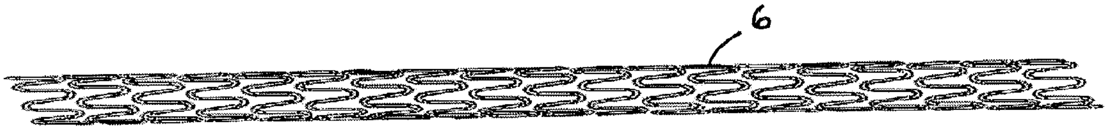
FIG. 2C is a cross-sectional view of the mid-plane of the wire frame of FIG. 2A in a compressive profile.
Figure 2D:
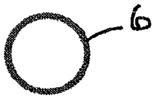
FIG. 2D is a transverse sectional view of the wire frame of FIG. 2A in a compressive profile.

FIG. 2A provides a cross-sectional view of a mid-plane of the Nitinol wire frame 6 in an expanded profile. The shape of wire frame 6 is preferably a combination of a zig-zag pattern and a helix. Wire frame 6 is strong in the radial direction to support the cannula or the vein, but remains axially flexible to easily comply with the curve of the vessel in which it is used. Wire frame 6 preferably has a maximum (i.e., expanded) diameter that fits the distal end of drainage cannula 4, and more particularly has a diameter that is slightly smaller than, and preferably 1 to 2 mm smaller than, the diameter of the patient's SVC. Thus, the system described herein may be provided in a series of sizes for use with differing patients (i.e., ranging from child to adult-sized patients). FIG. 2B is a transverse sectional view of wire frame 6 in an expanded profile. The profile is a circle in this view, although other profiles may be realized, such as a polygonal profile, without departing from the spirit and scope of the invention. FIG. 2C shows the same wire frame 6 in a compressed profile. This compressed profile may be achieved by applying forces around the circumferential surface of the wire frame of FIG. 2A. When using a superelastic material such as Nitinol, such compression is preferably carried out at a temperature below the transition temperature of wire frame 6. FIG. 2D is a transverse sectional view of wire frame 6 in a compressed profile. The diameter of wire frame 6 in a compressed profile may be between ⅓ and ⅔, and preferably between ½ and ⅔, of that of wire frame 6 in an expanded profile.

Figure 2E:
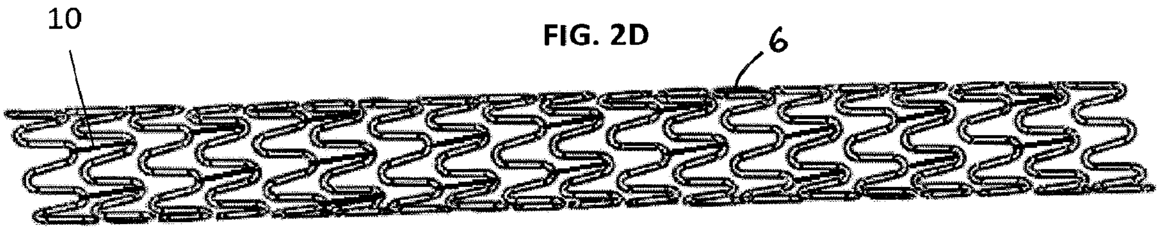
FIG. 2E is a cross-sectional view of the mid-plane of the wire frame of FIG. 2A in an expanded profile and including linkages.
Figure 2F:
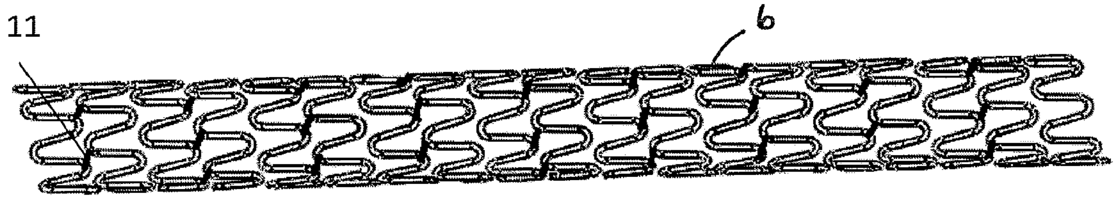
FIG. 2F is a cross-sectional view of the mid-plane of the wire frame of FIG. 2A in an expanded profile and including alternative linkages.

FIG. 2E and FIG. 2F are cross-sectional views of a mid-plane of wire frame 6 in an expanded profile showing additional, optional features. Those wire frames are configured similarly to the wire frame shown in FIG. 2A, with the addition of linkages (10 in FIGS. 2E and 11 in FIG. 2F) between neighboring segments of wire frame 6. Those linkages 10 and 11 may likewise be formed of Nitinol, and may be connected to the neighboring segments of wire frame 6 by, for example, laser welding. Those linkages 10 and 11 may provide additional strength in the axial direction, but still maintain some degree of flexibility for the wire frame 6.

Figure 2G:
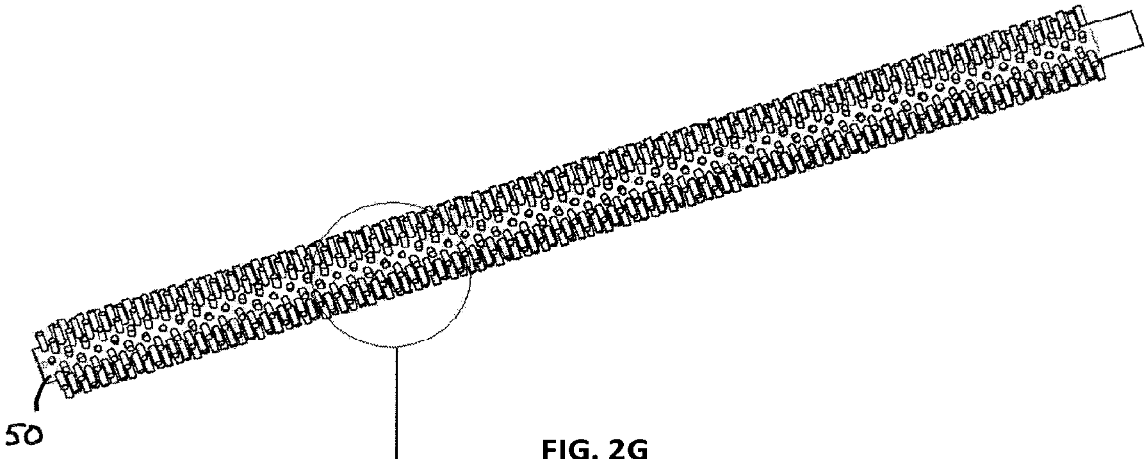
FIG. 2G is a perspective view of a mandrel used for fixing Nitinol wire in a heat treatment.
Figure 2H:
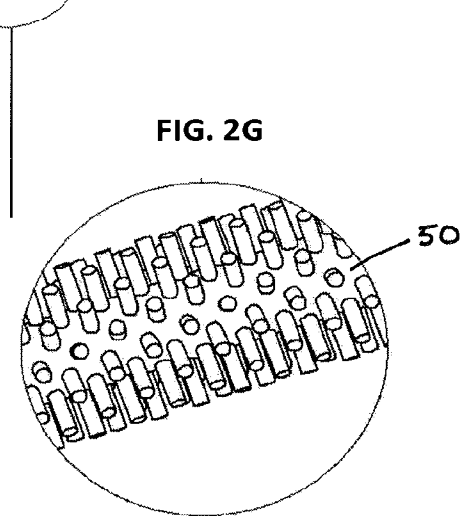
FIG. 2H is a partial enlarged view of the mandrel of FIG. 2G.

When comprised of a superelastic material such as Nitinol, wire frame 6 can be formed by firmly constraining the circular wire on the mandrel 50 shown in FIG. 2G and performing heat treatment as described above. FIG. 2H is a partial enlarged view of the mandrel 50 of FIG. 2G. The wire frame can also be manufactured from Nitinol tubes by laser cutting, such as through use of a 3D model made as may be created in SOLIDWORKS.

Figure 3A:
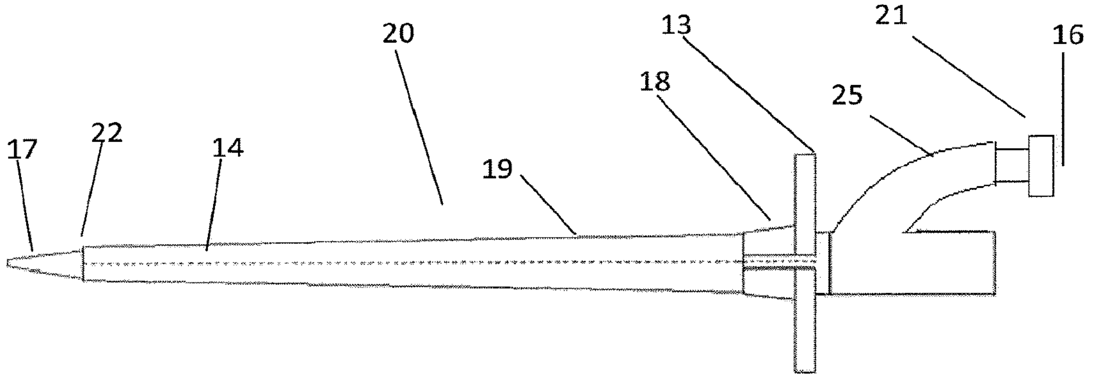
FIG. 3A is a side view of the DLC assembly of FIG. 1A including its delivery system.

FIG. 3A is a side view of the DLC assembly 1 packaged within its delivery system. The delivery system includes a tearable sheath 20 and an introducer 21. The tearable sheath 20 consists of a sheath body 19 and a head portion 18 attached to sheath body 19. Wings 13 may be provided on opposite sides of head portion 18. Tearable sheath 20 may be torn into two parts along its center line 14 (which may be provided a weakened line or section, such as by perforation) by pulling the wings 13 in opposite directions. The sheath body 19 is tapered and is smaller at the distal end 22 of sheath body 19.

Figure 3B:
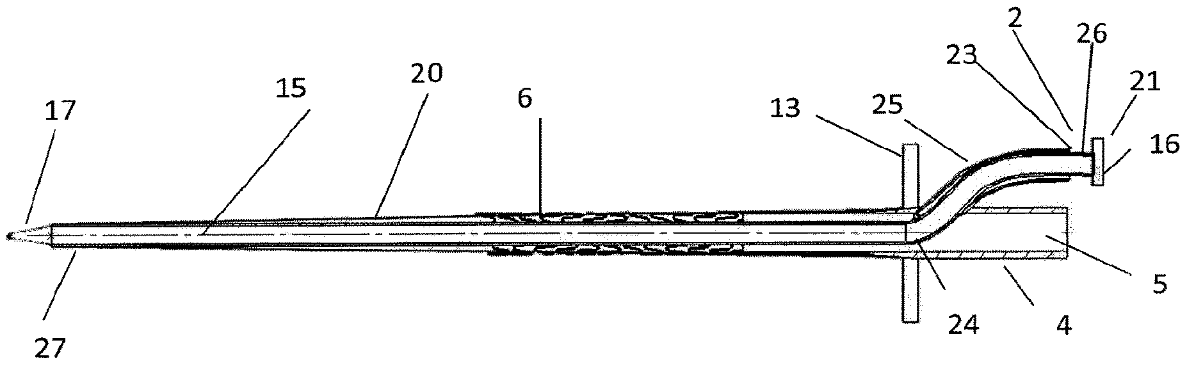
FIG. 3B is a cross-sectional view of the DLC assembly and its delivery system of FIG. 3A.

FIG. 3B is a cross-sectional view of DLC assembly and its delivery system. The introducer 21 includes a body 15, a circular handle 16 and a tapered tip 17. In some embodiments, the introducer body 15 is a cylinder. In other embodiments, the introducer body 15 is a cone. The introducer 21 is an atraumatic and flexible body having a small lumen extending longitudinally through the introducer, which may be used, for example, for passage of a guide wire. The introducer 21 may be placed in the infusion cannula 2 and is configured to slide easily in the infusion cannula 2. Because the diameter of circular handle 16 of the introducer 21 is larger than the inner diameter of infusion lumen 3, the introducer 21 will stop when handle 16 reaches the proximal end 26 of infusion cannula 2. Because of the self-expanding properties of wire frame 6 discussed above, wire frame 6 of the DLC assembly 1 can be squeezed radially, and may be positioned inside of tearable sheath 20 between the interior of tearable sheath 20 and the exterior of infusion cannula 2, maintaining its compressed shape. In certain embodiments in which wire frame 6 is formed of superelastic material such as Nitinol, wire frame 6 may be squeezed radially at a certain temperature below its transition temperature (e.g., at 11° C. in one embodiment).

The length by which a portion 23 of infusion cannula 2 will remain extending proximally from infusion port 25 may vary depending upon the function of DLC assembly 1. For some applications, the length of the portion 23 may be from 3 to 5 cm. In preferred embodiments, this will result in the distal end of diffusion cannula 2 extending outward from the distal end of wire frame 6 by preferably 10 to 15 cm. Those skilled in the art will recognize that the length of infusion cannula may vary for patients of differing sizes (e.g., children versus adult patients), so long as the system is dimensioned to perform as set forth herein.

Infusion cannula 2 enters the drainage lumen 5 from the infusion port 25. As shown in FIG. 3B, as infusion cannula 2 transitions from infusion port 25 towards the distal end of drainage cannula 4, it curves at a portion 24 of infusion cannula 2. Optionally, this portion 24 may be reinforced by a wire frame (not shown in FIG. 3B).

Infusion port 25 and drainage cannula 4 may be formed as a single part, such as by way of non-limiting example through injection molding or cast urethane using medical grade polyurethane with a shore hardness of 80 A. The thickness of drainage cannula 4 is preferably 1 to 2 mm. Infusion cannula 2 may be also formed of medical grade polyurethane or silicone. Infusion cannula 2 may be manufactured, by way of non-limiting example, through dip molding or extrusion, the methods for which are well known to those skilled in the art. The size of the drainage lumen 5 is preferably 18 to 34 Fr and its length is preferably 10 to 30 cm, and more preferably 20 to 30 cm. The size of the infusion lumen 3 is preferably 10 to 20 Fr and its length is preferably 40 to 45 cm. The distal tip 27 (FIG. 3B) of infusion cannula 2 is preferably radiopaque so that it can be seen in an x-ray or fluoroscopic image, which may be used for locating the cannula precisely during insertion. The DLC assembly 1 with the compressive wire frame 6, and with introducer 21 inserted, may be placed in a smaller diameter tearable sheath 20. The DLC assembly 1 and its delivery system are then ready to use.

Figure 4A:
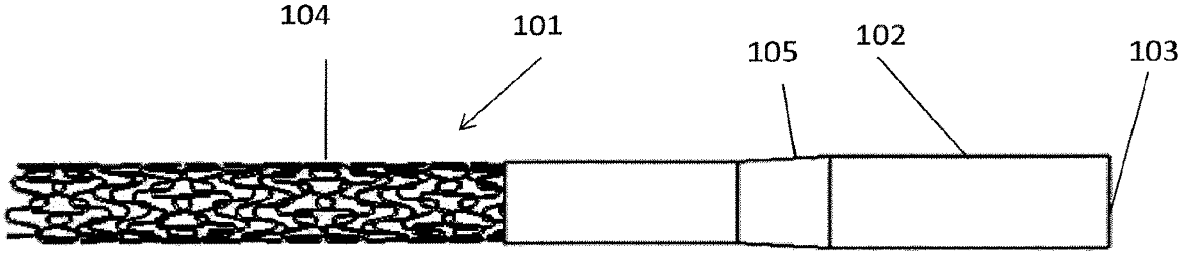
FIG. 4A is a side view of a SLC assembly according to aspects of the present invention.
Figure 4B:
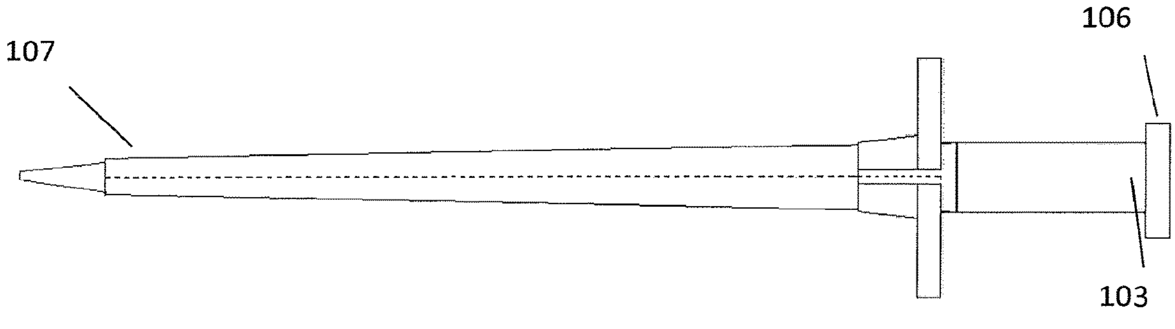
FIG. 4B is a side view of the SLC assembly of FIG. 4A including its delivery system.

FIG. 4A is a side view of an SLC assembly 101 in accordance with aspects of the invention. Its structure is similar to DLC assembly 1 shown in FIG. 1D, with the exception that it has only a single lumen 103. SLC 101 includes a cannula 102 with a tapered distal end 105 and forming lumen 103. An end of self-expanding wire frame 104 (configured as above) is preferably embedded in that tapered end 105 of cannula 102. FIG. 4B shows the SLC assembly 101 and its delivery system. Like DLC assembly 1 and its delivery system, SLC assembly 101 and its delivery system include a tapered, tearable sheath 107 and an atraumatic introducer 106. The introducer is inserted into the lumen 103 in cannula 102. When SLC assembly 101 is positioned within its delivery system, wire frame 104 is compressed as it sits within sheath 107. When cannula 102 and its delivery system are in position in a vessel, sheath 107 is torn (in like manner to sheath 20 described above), and the wire frame expands to support the vessel. Cannula 102 may be used as a venous drainage cannula.

In use, the DLC assembly 1 and its delivery system for Veno-PA ECMO may be inserted into the patient from the internal jugular vein. First, a balloon catheter (e.g., a Swan-Ganz catheter) may be inserted from the internal jugular vein. With the aid of an inflated balloon in its tip, the balloon catheter traverses through the right atrium and the right ventricle and reaches the pulmonary artery. After the catheter reaches the pulmonary artery, a guide wire can be placed through the lumen of the balloon catheter and up to the pulmonary artery, after which the balloon catheter may be withdrawn. Next, the DLC assembly 1 and its delivery system are inserted over the guide wire under fluoroscopy until the radiopaque distal tip 27 of the infusion cannula 2 reaches the right ventricle. At this point, the infusion lumen 2 is further advanced over the guide wire to the pulmonary artery, while the rest of the DLC assembly 1 and its delivery system are held in place. Once the infusion lumen 2 is positioned in the pulmonary artery, tearable sheath 20 is torn and withdrawn, simultaneously exposing the self-expanding wire frame 6. In embodiments in which wire frame 6 is comprised of Nitinol, because of its superelastic property, the compressed Nitinol wire frame 6 expands radially (in response to warming from the patient's body temperature to its transition temperature) to the wire frame's preset shape, and thereafter prevents collapsing of the SVC during draining blood. Alternatively, the wire frame may be sufficiently flexible to allow its radial compression by sheath 20 and automatically restore to its normal, uncompressed diameter when sheath 20 is removed. The wire frame 6 used here should be biocompatible so as to greatly reduce the possibility of thrombosis. Introducer 21 is then withdrawn, and a hemostatic seal (not shown in the figure) may be placed in the space between the infusion cannula 2 and the infusion port 25 to complete the insertion process.

While able to maintain the same flow rate as is available in prior art DLC configurations, this DLC with a self-expanding feature causes less trauma to the vessel compared to prior art DLC configurations because it is much smaller in the radial direction during insertion.

Depending upon the particular operation, the DLC assembly 1 and its delivery system may alternatively be inserted from the subclavian or femoral vein.

Figure 5A:
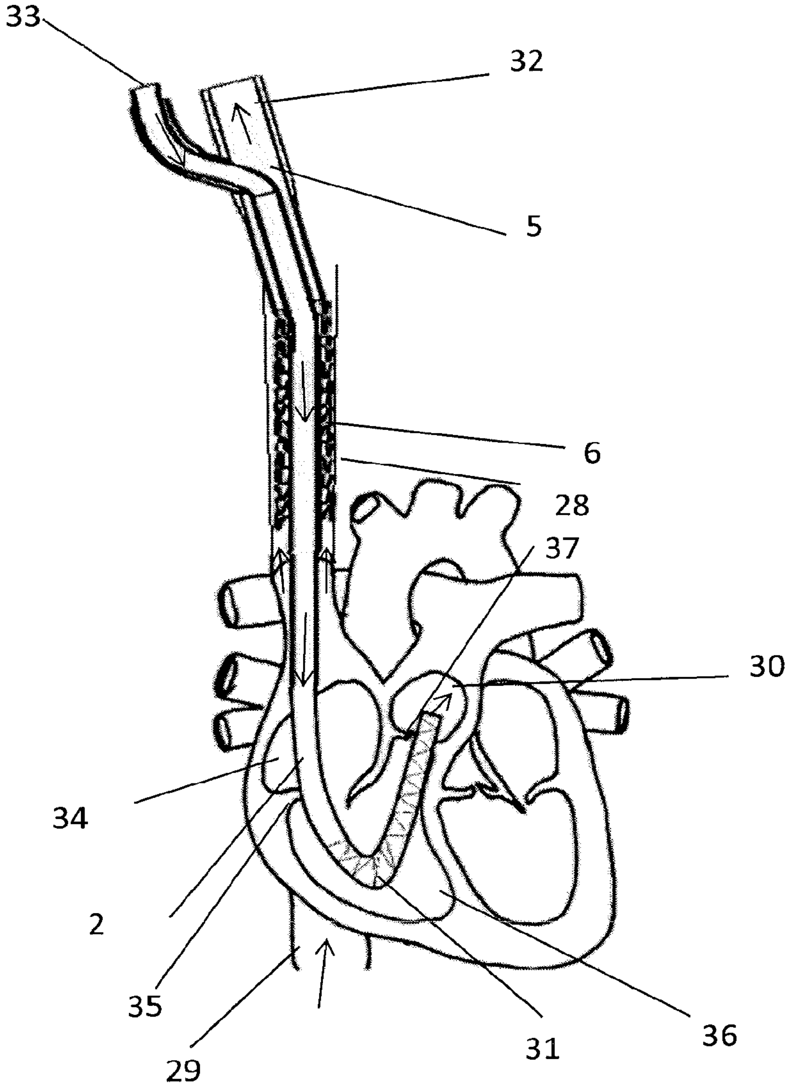
FIG. 5A is a schematic diagram of the DLC assembly of FIG. 1A and a patient's heart with the DLC assembly in position for Veno-PA ECMO.

FIG. 5A is a schematic diagram of the DLC assembly 1 embodying aspects of the invention, and a patient's heart with the DLC assembly 1 in position for Veno-PA ECMO. The SVC in this case will be used as a part of the drainage lumen. The DLC drains blood both upstream and downstream at the insertion site, thus avoiding long term obstruction of the SVC, which leads to thrombosis. The venous blood is drained from the SVC 28 and the IVC 29 and comes out of the patient's body from the outlet 32 of drainage lumen 5. Thereafter, the venous blood (oxygen poor blood) goes through a blood pump, an oxygenator and other associated devices (not shown in the figure) and becomes oxygenated blood (oxygen rich blood). The equipment and processes for the extracorporeal oxygenation of blood are well known to those skilled in the art and are thus not discussed further here. After oxygenation, the oxygenated blood travels back to the pulmonary artery 30 through the inlet 33 of infusion lumen 3. In the human body, the blood flows from the right atrium 34 through the tricuspid valve 35 to the right ventricle 36, and then goes through the pulmonary valve 37 to the pulmonary artery 30. The functions of the tricuspid valve 35 and the pulmonary valve 37 are both to prevent back flow. Placing the infusion lumen 2 directly into the pulmonary artery 30 reduces the blood recirculation to a great extent.

The preset diameter of the Nitinol wire frame 6 should be slightly smaller than the diameter of the SVC 28. When a negative pressure is applied on the drainage lumen 5, the SVC 28 shrinks as its walls collapse inward, and is supported by wire frame 6. When the negative pressure is removed, the SVC 28 will return to its original diameter. At this point, there is sufficient space between wire frame 6 and the SVC 28 so that the DLC system 1 can be withdrawn from the SVC.

Another wire frame 31 may be positioned in the infusion cannula 2 (such as by molding wire frame 31 into the wall of infusion cannula 2), which preferably is also formed of Nitinol, and its structure can be similar to that of the wire frame 6, or it may be helical. The section within the right ventricle can be pre-set as a curved shape as shown in FIG. 5A. Such additional wire frame 31 may be used to prevent the creation of a kink of the curved portion of the infusion cannula 2 in the right ventricle.

Figure 5B:
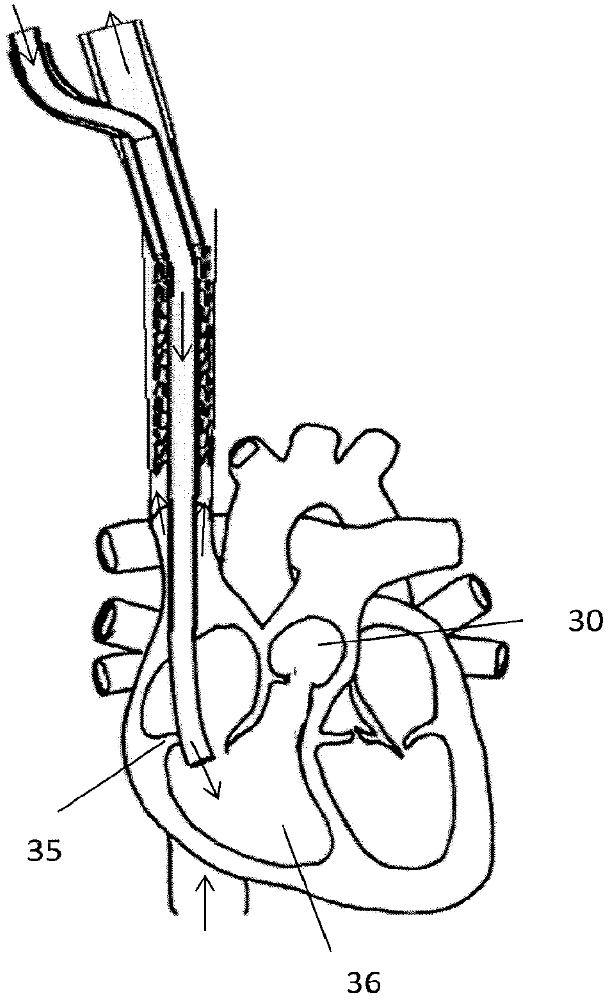
FIG. 5B is a schematic diagram of the DLC assembly of FIG. 1A and a patient's heart with the DLC assembly in position for Veno-RV ECMO.

FIG. 5B is a schematic diagram of the DLC assembly of the invention and a patient's heart, with the DLC assembly in position for Veno-RV ECMO. This application is similar to the one described above with reference to FIG. 5A. One difference, however, is that the infusion lumen is placed in the right ventricle 36 as opposed to the pulmonary artery 30. Another difference is that the Nitinol wire frame 31 in the infusion cannula 2 in FIG. 5A is not needed for this DLC. Because of the tricuspid valve 35, the blood recirculation is very low.

Figure 5C:
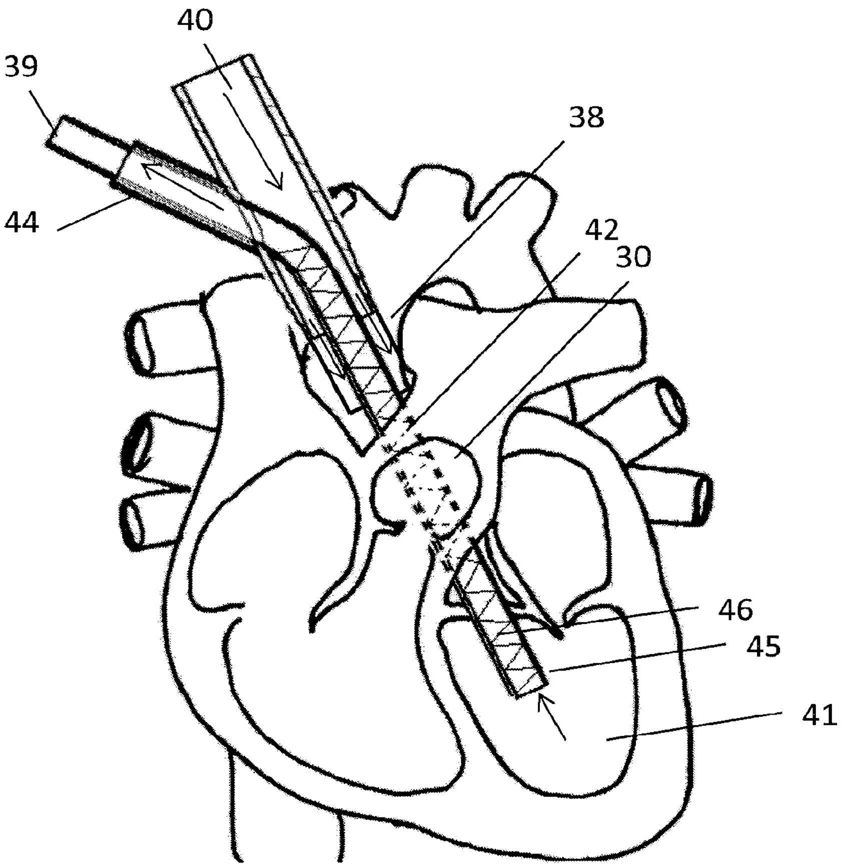
FIG. 5C is a schematic diagram of a DLC assembly according to further aspects of the invention and a patient's heart with the DLC assembly in position for LV-Aortic mode LVAD support.

FIG. 5C is a schematic diagram of the DLC assembly of the invention and heart with the DLC assembly in position for LV-Aortic mode LVAD. The DLC assembly is inserted from the ascending aorta 38 or descending aorta (not shown) by minimally-invasive surgery. Different from the previous cases, the drainage lumen 39 has a smaller diameter than the infusion lumen 40. The location of distal end 45 of the drainage lumen 39 can be adjusted by moving it in the drainage port 44. In this case, the drainage cannula should have a length sufficient so that distal end 45 of drainage lumen 39 may be positioned in the patient's left ventricle 41 when the distal end of the infusion lumen 40 is positioned in the ascending aorta 38. The arterial blood in the left ventricle 41 is drawn by a blood pump (not shown in the figure) through the drainage lumen 39 and returns to the ascending aorta 38 through the infusion lumen 40. As shown in FIG. 5C, the portion 42 of the cannula and self-expanding wire frame (such as a Nitinol wire frame) in the ascending aorta 38 and behind the pulmonary artery 30 is shown in dashed lines. In this configuration, the wire frame is completely embedded inside the wall of the drainage cannula and provides radial support to the drainage cannula as blood is suctioned through drainage lumen 39. The shape of the wire frame 46 in this configuration is preferably helical, but may likewise embody a shape similar to that of the wire frame 6 in FIG. 5A.

For traditional LVAD, blood is drained from the left ventricle 41 through a cannula by a pump and infused back to the aorta through another cannula, requiring multiple cannulation. The application shown in FIG. 5C utilizing aspects of the instant invention avoids multiple cannulation and reduces trauma and difficulty of surgery.

The self expanding cannula system employing aspects of the invention provides significant benefits over the prior, which in each application may include one or more of the following: (i) the avoidance of multiple cannulation; (ii) minimally invasive insertion and self-expansion when placed in position in a patient's body; (iii) a lessening of blood and vessel trauma; (iv) a lessening of the possibility of thrombosis; (v) avoidance of major invasive surgery; and (vi) minimal blood recirculation.

Having now fully set forth the preferred embodiments and certain modifications of the concepts underlying the present invention, various other embodiments as well as certain variations and modifications of the embodiments herein shown and described will obviously occur to those skilled in the art upon becoming familiar with said underlying concepts. It should be understood, therefore, that the invention may be practiced otherwise than as specifically set forth herein.

INDUSTRIAL APPLICABILITY

The present invention is applicable to medical devices, and particularly to cannulae, systems using cannulas and methods for their use. The devices can be made in industry and practiced in the medical device field.

What is claimed is:

1. A system for fluid handling of a patient's blood, comprising:

a first cannula having a distal first cannula end and a proximal first cannula end opposite said distal first cannula end, said distal first cannula end having a tapered wall portion;

a self-expanding wire frame defining an open face at a distal wire frame end and having a proximal wire frame end opposite said distal wire frame end, said proximal wire frame end being embedded within said tapered wall portion of said distal first cannula end, said wire frame comprising a continuous helical and zig-zag pattern, said wire frame having a first diameter and being automatically expandable to a maximum diameter when positioned to collect blood from the patient's body, wherein said maximum diameter is selected to be 1 to 2 mm smaller than a diameter of the patient's superior vena cava, wherein said open face is expandable to said maximum diameter of said wire frame and wherein the first cannula and the self-expanding wire frame together form a blood withdrawal lumen; and a second cannula having a distal second cannula end and a proximal second cannula end opposite said distal second cannula end, said second cannula having an outer diameter sized to allow said second cannula to be positioned in and to move within said first cannula and said wire frame, wherein said second cannula forms a blood infusion lumen extending coaxially through said blood withdrawal lumen.

2. The system of claim 1, wherein said self-expanding wire frame is automatically expandable to said maximum diameter in response to warming from the patient's body temperature.

3. The system of claim 2, said wire frame being compressible to a reduced diameter when exposed to a temperature less than a human's normal body temperature, said reduced diameter being sufficiently small to allow passage of said wire frame through a portion of the patient's circulatory system.

4. The system of claim 1, said maximum diameter being selected so as to provide radial support to a vessel in which said wire frame is positioned against collapse during suctioning of blood through said wire frame and said first cannula.

5. The system of claim 1, wherein said distal first cannula end tapers toward a reduced diameter at a distal face of said distal first cannula end.

6. The system of claim 1, further comprising linkages between longitudinally adjacent segments of said zig-zag pattern.

7. The system of claim 1, further comprising a port extending into a sidewall of said first cannula.

8. The system of claim 7, wherein said second cannula is further configured to allow said second cannula to be positioned in and to move within said port, said first cannula and said wire frame.

9. The system of claim 8, wherein said distal second cannula end is radio-opaque.

10. The system of claim 8, said second cannula further comprising a second wire frame embedded within the distal second cannula end.

11. The system of claim 10, wherein said second wire frame is automatically expandable from a reduced second wire frame diameter to an enlarged second wire frame diameter in response to warming from the patient's body temperature.

12. The system of claim 8, further comprising a sheath having a distal sheath having an internal diameter selected to allow said first cannula, said wire frame, and said second cannula to be positioned within said sheath.

13. The system of claim 12, wherein said self-expanding wire frame is sufficiently flexible so as to radially compress to a reduced diameter when said first cannula, said wire frame, and said second cannula are positioned within said sheath and to automatically expand to said maximum diameter upon removal of said sheath.

14. The system of claim 12, said sheath having a line of weakening extending along a longitudinal length of said sheath and configured to allow said sheath to be removed from said first cannula, said wire frame, and said second cannula after placement of said first cannula, said wire frame, said second cannula within a blood vessel of the patient.

15. The system of claim 12, further comprising an introducer having an outer diameter sized to allow said introducer to extend through said second cannula toward and through said distal second cannula end.

16. The system of claim 15, said introducer having a tapered, distal introducer end.

17. The system of claim 8, wherein said distal second cannula end is distally positionable a sufficient distance away from said distal wire frame end so as to prevent extracorporeal recirculation of fluid that has been drained from and returned to the patient by the system.

* * * * *